(12) United States Patent
Andjelic et al.

(10) Patent No.: US 9,873,790 B1
(45) Date of Patent: Jan. 23, 2018

(54) ABSORBABLE POLYMER BLEND COMPOSITIONS HAVING ENHANCED NUCLEATION RATES

(71) Applicant: Ethicon, Inc., Somerville, NJ (US)

(72) Inventors: Sasa Andjelic, Nanuet, NY (US); Kenneth Keilman, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 15/345,034

(22) Filed: Nov. 7, 2016

(51) Int. Cl.
| | | |
|---|---|---|
| *C08L 67/04* | (2006.01) | |
| *C08G 63/664* | (2006.01) | |
| *C08J 3/00* | (2006.01) | |
| *C08G 63/08* | (2006.01) | |
| *A61L 27/26* | (2006.01) | |
| *A61L 27/18* | (2006.01) | |
| *A61L 31/04* | (2006.01) | |
| *A61L 31/06* | (2006.01) | |
| *A61K 47/34* | (2017.01) | |
| *C08G 63/02* | (2006.01) | |

(52) U.S. Cl.
CPC .............. *C08L 67/04* (2013.01); *A61K 47/34* (2013.01); *A61L 27/18* (2013.01); *A61L 27/26* (2013.01); *A61L 31/041* (2013.01); *A61L 31/06* (2013.01); *C08G 63/08* (2013.01); *C08G 63/664* (2013.01); *C08J 3/005* (2013.01); *C08J 2367/04* (2013.01); *C08J 2467/04* (2013.01); *C08L 2203/02* (2013.01); *C08L 2205/025* (2013.01)

(58) Field of Classification Search
CPC ................................................... C08L 67/04
USPC .................................. 525/411, 415; 528/354
See application file for complete search history.

(56) References Cited

U.S. PATENT DOCUMENTS

| | | |
|---|---|---|
| 5,539,076 A | 7/1996 | Nowlin et al. |
| 6,794,484 B2 | 9/2004 | Newman, Jr. et al. |
| 6,831,149 B2 | 12/2004 | Newman, Jr. et al. |
| 8,450,431 B2 | 5/2013 | Andjelic et al. |
| 9,238,094 B2 | 1/2016 | Andelic et al. |

OTHER PUBLICATIONS

Cheng, S.Z.D. et al., "Molecular Segregation and Mucleation of Poly(ethylene Oxide) Crystallized from the Melt. II. Kinetic Study". Journal of Polymer Science: Part B: Polymer Physics, vol. 24, pp. 595-617 (1986).
Fernandez-Ballester, L, Thurman et al. "Effect of Long Chains on the Threshold Stresses for Flow-Induced Crystallization in iPP: Shish Kebabs vs. Sausages". Macromolesules, (2012), vol. 45, pp. 6557-6570.
Yeh, G.S.Y. et al. "Strain-Induced Crystallization, Part III: Theory". Polymer Engineering and Science, (mid-May 1979), vol. 19, No. 6, pp. 395-400.
Yeh, G.S.Y. "Strain-Induced Crystallization II. Subsequent Fibrillar-to-lamellar Transformation". Polymer Engineering and Science, (Mar. 1976), vol. 16, No. 3, pp. 145-151.
Yeh, G.S.Y. "Strain-Induced Crystallization I. Limiting Extents of Strain-Induced Nuclei". Polymer Engineering and Science, (Mar. 1976)., vol. 16, No. 3, pp. 138-144.
Lopez, J.M. Rego et al. "Crystallization of binary linear polyethylene blends". Polymer, (1988) vol. 29, June, pp. 1045-1051.
Chen, Y.H. et al. "Competitive Growth of a-and b-crytals in b-Nucleated Isotactic Polypropylene under Shear Flow". Macromolesules (2010), vol. 43, pp. 6760-6771.
Seki, M. et al. "Shear-Mediated Crystallization of Isotactic Polypropylene: The Role of Long Chain—Long Chain Overlap". Macromolecules (2002), vol. 35, pp. 2583-2594.

*Primary Examiner* — Terressa Boykin
(74) *Attorney, Agent, or Firm* — E. Richard Skula

(57) ABSTRACT

Novel absorbable, semi-crystalline, polymer blend compositions are disclosed exhibiting enhanced crystallization and nucleation rates. Also disclosed are medical device constructs, such as fibers made from such blends. The blends have a first absorbable polymeric component having a first molecular weight distribution and a second absorbable polymeric component which has an ultrahigh molecular weight distribution. The first and second polymeric components may be the same polymer.

24 Claims, 3 Drawing Sheets
(3 of 3 Drawing Sheet(s) Filed in Color)

Isothermal Crystallization rates of Poly(*p*-dioxanone), PDS, and Ultrahigh Molecular Weight PDS, UHMWPDS, as Controls, and their PDS/UHMWPDS Blends

*In vitro* BSR Properties of PDS Control Fiber and Inventive PDS/UHMWPDS Fiber Blend Compositions

Isothermal Crystallization Rates of 75/25 Lac/Cap Copolymer and Inventive [75/25 Lac/Cap]/UHMWPLLA Blend

US 9,873,790 B1

ABSORBABLE POLYMER BLEND COMPOSITIONS HAVING ENHANCED NUCLEATION RATES

FIELD

The field of art to which this invention relates is novel absorbable polymer blend compositions and, more particularly, to absorbable polymer blend compositions having ultrahigh molecular weight of the same or similar chemical structure as a minor component, to medical devices produced therefrom and to methods of making absorbable polymer blend compositions.

BACKGROUND OF THE INVENTION

Synthetic absorbable polyesters are well known in the art. The terms absorbable, bioabsorbable, bioresorbable, resorbable, biodegradable are used herein interchangeably. The open and patent literature particularly describe polymers and copolymers made from glycolide, L(−)-lactide, D(+)-lactide, meso-lactide, epsilon-caprolactone, p-dioxanone, and trimethylene carbonate.

Of particular interest are those synthetic absorbable polyesters that are semicrystalline in nature, due to their enriched and enhanced mechanical properties. A certain degree of crystallinity of polymer components is often desired during injection molding or extrusion operations due to the higher thermal and mechanical stability associated therewith. If the crystallization rate of an absorbable polymer component is slow or uneven, the resultant product properties may have a wide variation in morphology, creating a potential for lines of imperfection that may lead to material failure and result in lower production capacity and reduced quality of the final product. The ability of a polymer system to crystallize quickly is particularly important for processing, especially for injection molding. The faster that an article crystallizes in a mold, the shorter the cycle time that is needed for developing a morphology that demonstrates increased dimensional stability and avoids or minimizes warping. While there is an economic benefit in reduced cycle time, shortened cycle times also reduce the time the polymer resides in the molding machine at elevated temperatures. This reduces the amount of thermal degradation effects such as molecular weight reduction and discoloration that may occur, further improving molded part quality. Retention of a desired molecular weight may additionally lead to better mechanical properties, and in the case of molded parts intended for surgical implantation, the retention of molecular properties post-implantation. The amount of crystallinity needed in the part prior to ejection from the mold depends on the glass transition temperature of the resin as well as the molecular weight of the resin. For example, the lower the glass transition temperature, the higher the level of crystallinity that is needed to provide dimensional stability in a molded part.

In some cases, it is advantageous to have the molded part crystallize outside the mold, that is, after the part has been ejected from the molding machine. The ability for the part to crystallize at a rapid rate is advantageous from a processing standpoint. Rapid crystallization is very helpful in providing dimensional stability of the part as it is undergoing further processing. Beside the rate or kinetics of crystallization, the ultimate level of crystallinity developed in the part is also of great importance. If the ultimate level of crystallinity developed in the part is insufficient, the part may not possess the dimensional stability required.

In order to increase the rate of crystallization of a polymer, one must increase either the steady-state concentration of nuclei in the polymer matrix, or increase the rate of crystal growth. In general, an increase in nucleation density can be readily accomplished by adding nucleating agents that are either physical (inactive) or chemical (active) in nature. An introduction of foreign particles can also serve as a nucleation agent. For example, with regard to the absorbable polymers used by the medical industry, such agents can include starch, sucrose, lactose, fine polymer particles of polyglycolide and copolymers of glycolide and lactide, which may be used, for example, during the manufacturing of surgical fasteners or during subsequent fiber processing. Other ways to increase the nucleation rate without the addition of foreign-based materials include copolymerization with a stiffer, highly crystallizable component, preserving nucleating seeds of a faster crystallizing component during melt manufacturing steps, stress-induced nucleation, the use of magnetic field strength, or sonic-based energy, as used by the pharmaceutical industry.

The use of specific ratios of mono- to bi-functional initiators in the ring-opening polymerization of glycolide-containing absorbable copolyesters has been described in the patent literature (U.S. Pat. No. 6,794,484 B2 and U.S. Pat. No. 6,831,149 B2). These systems provide enhanced nucleation rates, but do not affect the spherulitic growth of an absorbable glycolide-containing polymeric material.

It has been proposed in U.S. Pat. No. 5,539,076 that bimodal molecular weight distributions may be employed for polyolefins to enhance polymer processing, and reduce the tendency of die-lip polymer buildup and smoking in on-line operations. Moreover, the crystallization behavior of various binary compositions has been reported for linear polyethylene blends in *Polymer*, 1988, 29(6), 1045. This study suggests that the two fractions of a binary linear polyethylene blend crystallize separately and independently at moderate and high temperatures and partially co-crystallize at lower temperatures. Similarly, Cheng and Wunderlich, in *J. Polym. Sci. Polym. Phys.*, 1986, 24, 595 and *J. Polym. Sci. Polym. Phys.*, 1991, 29, 515, reported on their crystallization kinetic studies of fractions of poly(ethylene oxides) between 3,500 and 100,000 Mw and their binary mixtures from the melt. These studies suggested that mixed-crystal formation at low crystallization temperatures occurred, with increasing segregation at higher temperatures, despite the higher deposition probabilities of the low molecular weight component.

U.S. Pat. Nos. 8,450,431 B2 and 9,238,094 B2, incorporated herein by reference in their entirety, and their related applications disclose bimodal bioabsorbable polymer compositions. The compositions include a first amount of a bioabsorbable polymer polymerized so as to have a first molecular weight distribution; a second amount of the same bioabsorbable polymer polymerized so as to have a second molecular weight distribution having a weight average molecular weight between about 10,000 to about 50,000 Daltons, wherein the weight average molecular weight ratio of said first molecular weight distribution to said second molecular weight distribution is at least about two to one. A substantially homogeneous blend of the first and second amounts of the bioabsorbable polymer is formed in a ratio of between about 50/50 to about 95/5 weight/weight percent. These semi-crystalline polymer blends have been shown to significantly increase one part of the crystallization mechanism, that is, a spherulitic growth. Nucleation, on the other hand, is not affected or altered by these bimodal blends.

It has been also known in the art that the application of strain to a polymer melt is likely to increase its crystallization kinetics [Yeh, G. S. Y., Polymer Engineering and Science 16, 138 1976; Yeh, G. S. Y., Polymer Engineering and Science 16, 145 1976; Yeh, G. S. Y.; Hong, K. Z., Polymer Engineering and Science 19, 395 1979]. This phenomenon is usually referred to as "Strain or Flow Induced Crystallization". The phenomenon is observed in many semicrystalline polymer systems, including polyethylene, polypropylene, other polyolefins, polyethers, and polyesters. Interestingly, several studies [Fernandez-Ballester, L.; Thurman, D. W.; Zhou, W.; Kornfield, J. A., Macromolecules 45, 6557 2012; Seki, M.; Thurman, D. W.; P., O. J.; Kornfield, J. A., Macromolecules 35, 2583 2002; Chen, Y.-H.; Mao, Y.-M.; Li, Z.-M.; Hsaio, B. S., Macromolecules 43, 6760 2010] showed that the addition of a small quantity of ultrahigh molecular weight polyolefin, isotactic polypropylene (i-PP), to a matrix of lower molecular weight i-PP resulted in about a 10-fold increase in the crystallization kinetics when shear was applied to the polymer melt. However, there have been no studies describing the use of absorbable polyester systems with ultrahigh molecular weight seeds, and their impact on quiescent (non-shear) and shear induced polymer processing.

Despite these advances in the art, there is still a strong need for improved absorbable polymer systems having increased crystallization rates for further improvement in polymer processing. Thus, it would be desirable to provide advanced absorbable polymers having increased nucleation rates, especially those compositions without glycolide units present, and methods for their production.

SUMMARY OF THE INVENTION

Disclosed herein are novel compositions and methods of enhancing the crystallization rates via enhanced nucleation mechanism for absorbable materials. Also disclosed are methods of preparation of absorbable polymer compositions, the compositions so prepared possessing significantly higher crystallization kinetics and devices produced from such compositions. More specifically disclosed herein are absorbable polymeric blend compositions, processes of making the absorbable polymeric blend compositions and medical devices produced from such absorbable polymeric blend compositions.

One aspect of the present invention is an absorbable semi-crystalline polymer blend composition. The polymer blend composition has a first amount of a first absorbable polymer having a first crystallization rate, a first molecular weight distribution and a weight average molecular weight from about 50,000 to about 200,000 Daltons. The polymer blend composition also has a second amount of a second absorbable ultrahigh molecular weight polymer having a second crystallization rate, a second molecular weight distribution and a weight average molecular weight from about 300,000 to about 3,000,000 Daltons. The weight average molecular weight ratio of the first molecular weight distribution to the second molecular weight distribution is at least about one to three and a substantially homogeneous blend of said first and second components is formed in a ratio of between about 99.9/0.1 to about 95/5 weight/weight percent. The substantially homogeneous blend has a crystallization rate greater than each of said first crystallization rate and said second crystallization rate.

Another aspect of the present invention is a novel medical device comprising an absorbable semi-crystalline polymer blend composition. The polymer blend composition has a first amount of a first absorbable polymer having a first crystallization rate, a first molecular weight distribution and a weight average molecular weight from about 50,000 to about 200,000 Daltons. The polymer blend composition also has a second amount of a second absorbable ultrahigh molecular weight polymer having a second crystallization rate, a second molecular weight distribution and a weight average molecular weight from about 300,000 to about 3,000,000 Daltons. The weight average molecular weight ratio of the first molecular weight distribution to the second molecular weight distribution is at least about one to three and a substantially homogeneous blend of said first and second components is formed in a ratio of between about 99.9/0.1 to about 95/5 weight/weight percent. The substantially homogeneous blend has a crystallization rate greater than each of said first crystallization rate and said second crystallization rate.

Yet another aspect of the present invention is a method of making an absorbable semi-crystalline polymer blend. The method has the step of melt processing an absorbable polymer blend composition. The polymer blend composition has a first amount of a first absorbable polymer having a first crystallization rate, a first molecular weight distribution and a weight average molecular weight from about 50,000 to about 200,000 Daltons. The polymer blend composition also has a second amount of a second absorbable ultrahigh molecular weight polymer having a second crystallization rate, a second molecular weight distribution and a weight average molecular weight from about 300,000 to about 3,000,000 Daltons. The weight average molecular weight ratio of the first molecular weight distribution to the second molecular weight distribution is at least about one to three and a substantially homogeneous blend of said first and second components is formed in a ratio of between about 99.9/0.1 to about 95/5 weight/weight percent. The substantially homogeneous blend has a crystallization rate greater than each of said first crystallization rate and said second crystallization rate.

Still yet another aspect of the present invention is a method of making a medical device. The method has the step of forming a medical device by melt-processing or heat treating an absorbable semi-crystalline polymer blend over a temperature range of between about 80° C. to about 260° C. The polymer blend composition has a first amount of a first absorbable polymer having a first crystallization rate, a first molecular weight distribution and a weight average molecular weight from about 50,000 to about 200,000 Daltons. The polymer blend composition also has a second amount of a second absorbable ultrahigh molecular weight polymer having a second crystallization rate, a second molecular weight distribution and a weight average molecular weight from about 300,000 to about 3,000,000 Daltons. The weight average molecular weight ratio of the first molecular weight distribution to the second molecular weight distribution is at least about one to three and a substantially homogeneous blend of said first and second components is formed in a ratio of between about 99.9/0.1 to about 95/5 weight/weight percent. The substantially homogeneous blend has a crystallization rate greater than each of said first crystallization rate and said second crystallization rate.

A further aspect of the present invention is a method of manufacturing a polymeric blend. A first amount of a first absorbable polymer having a first crystallization rate, a first molecular weight distribution and a weight average molecular weight from about 50,000 to about 200,000 Daltons is provided. A second amount of a second absorbable ultrahigh molecular weight polymer having a second crystallization rate, a second molecular weight distribution and a weight average molecular weight from about 300,000 to about 3,000,000 Daltons is also provided. The weight average molecular weight ratio of the first molecular weight distribution to the second molecular weight distribution is at least about one to three. The first and second amounts are dry blended to form a blend. The blend is dried to remove moisture. The blend is melt blended to homogeneously distribute the second amount of the second polymer in the first amount of the first polymer to form a substantially homogenous blend in a ratio of between about 99.9/0.1 to about 95/5 weight/weight percent. The substantially homogeneous blend has a crystallization rate greater than each of the first crystallization rate and the second crystallization rate. The homogeneous blend is dried to remove moisture and residual monomer.

These and other aspects and advantages of the present invention will become more apparent from the following description and accompanying drawings.

BRIEF DESCRIPTION OF THE DRAWINGS

The patent or application file contains at least one drawing executed in color. Copies of this patent with color drawing(s) will be provided by the Patent and Trademark Office upon request and payment of necessary fee.

DETAILED DESCRIPTION OF THE INVENTION

Figure 1:
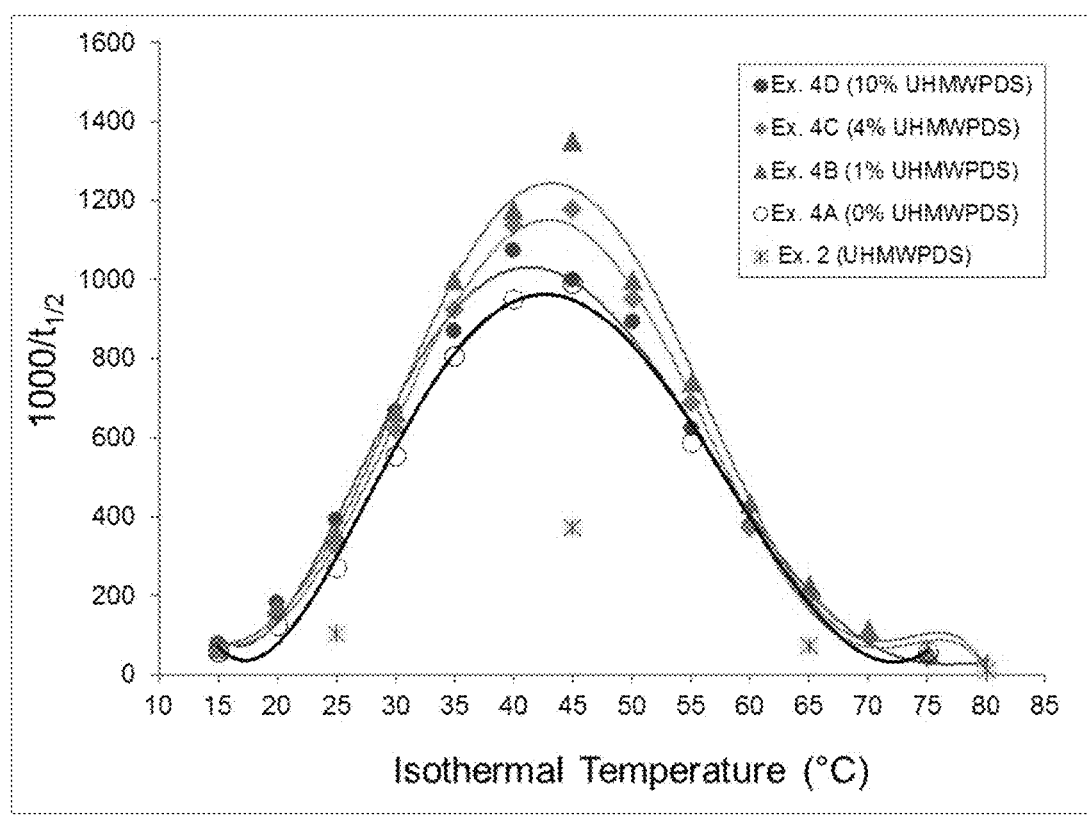
FIG. 1 is a graph that presents isothermal crystallization rates of poly(p-dioxanone), PDS and ultrahigh molecular weight PDS, UHMWPDS as controls, and their PDS/UHMWPDS blends.

The crystallization behavior of commercially important absorbable poly(p-dioxanone) homopolymers and copolymers have been studied extensively, and is well documented in numerous reports in the open literature [e.g. "Crystallization Study of Absorbable Poly(p-dioxanone) Polymers by Differential Scanning Calorimetry", Saša Andjelić, Dennis Jamiolkowski, James McDivitt, Jerome Fischer, Jack Zhou, Robert Vetrecin, Journal of Applied Polymer Science 2001, 79, 742-759; "Spherulitic Growth Rates and Morphology of Absorbable Poly(p-dioxanone) Homopolymer and its Copolymers by Hot-Stage Optical Microscopy", Saša Andjelić, Dennis Jamiolkowski, James McDivitt, Jerome Fischer, Jack Zhou, Journal of Polymer Science: Part B: Polymer Physics 2001, 39, 3073; "Time resolved study of shear-induced crystallization of poly(p-dioxanone) polymers under low-shear, nucleation-enhancing shear conditions by small angle light scattering and optical microscopy" Ferass Abuzaina, Benjamin Fitz, Saša Andjelić, Dennis Jamiolkowski, Polymer, 43, 4699, 2002]. Crystallization rates of absorbable poly(p-dioxanone) homopolymer, or PDS, have been described as slow, especially for its nucleation part, making the polymer processing of this material often difficult and non-economical.

Similarly, high molecular weight poly(L(−)-lactide), or PLLA, and its high lactide-containing copolymers are known to crystallize even more slowly, if at all, due to the reduced mobility of its highly entangled macromolecules. In addition, methyl side groups produce chain asymmetry causing nucleation to be particularly challenging. The crystallinity of different molecular weight PLLA homopolymers (18,000, 31,000, 156,000 and 425,000 g/mol) has been studied by calorimetric methods (see: *Clinical Materials*, 1991, 8(1-2), 111). As demonstrated by that study, during cooling from the melt (rate=−0.5° C./min), only the lower molecular weight polymers were able to develop any measurable crystallinity.

Both the PDS and the PLLA classes of absorbable materials have been extensively used in various, regulated medical applications. The potential addition of foreign particles as nucleation agents may be undesirable in that it may cause regulatory issues, problems with biocompatibility, initiate degradation reactions during high temperature polymer processes, and produce phase separation due to chemical incompatibility.

The novel blend compositions of the present invention described herein do not introduce foreign particles while providing significantly higher crystallization rates over and above the crystallization rates of the individual components.

As used herein, the term "ultrahigh molecular weight polymer" is defined to mean a polymer having a weight average molecular weight of at least 300,000 Daltons or above. Such high molecular weight values prevent regular melt processing operations due to its very high melt viscosity. In the case of absorbable ultrahigh molecular weight polymers, referred to as UHMW polymers, increasing the processing temperature to extreme high values will induce degradation reactions before the UHMW polymer starts to flow. Due to its long macromolecular chains and therefore slow macromolecular mobility, UHMW polymers are generally regarded as very slow-to-crystallize materials.

The novel absorbable polymer compositions of the present invention comprise physical blends of regular-to-high molecular weight absorbable polymers as a major component with a very small amount of an ultrahigh molecular weight counterpart of the same or similar polymer as a minor component. The polymer blends of this invention form semi-crystalline materials which have enhanced processability during melt-processing, including melt blending, extruding, melt spinning, melt blowing or injection molding. The blending of the individual components is conducted at a temperature above their melting temperatures, followed by cooling and crystallizing the resulting blend, while exhibiting synergistically faster crystallization kinetics as compared to the individual blend components alone. As will be shown later in the examples herein, the presence of the minor ultrahigh molecular weight polymer does not affect the spherulitic growth of the original material, but greatly increases the nucleation density of the polymer.

The term increased crystallization, as used herein, relates to the improvement in the crystallization properties of a polymer, yielding a polymer that crystallizes at a faster rate. Crystallizing at a faster rate has advantages when melt processing the polymers disclosed herein. This is especially true when fabricating medical devices utilizing melt or thermal processes such as using an injection molding or fiber extrusion process. Rapid crystallization is particularly advantageous when injection molding articles from resins with low glass transition temperatures, since dimensional stability is usually achieved by crystallization. In the absence of sufficiently effective crystallization, injection molded parts made from polymers possessing low glass transition temperatures also frequently display distortion and deformation upon removal from the mold, as they are not able to withstand the forces exerted during the removal process. As polymeric articles crystallize faster, cycle times correspondingly may be decreased. Not only are there potential economic advantages resulting from the attendant decreased production costs, but faster cycle times also reduce the time the polymer resides in the machine at elevated temperatures. This reduces the amount of degradation that may occur, further improving part quality. The amount of crystallinity needed in the part prior to ejection from the mold depends on the glass transition temperature of the resin as well as the molecular weight of the resin. The lower the glass transition temperature, the higher the level of crystallinity required. It has been found that it is advantageous to have a crystallinity level of at least 10% for some synthetic absorbable polymers possessing low glass transition temperatures. In the case of fibers of higher molecular orientation, the level of crystallinity required is correspondingly higher; at least about 15% and desirably greater than about 25% may be necessary to provide dimensional stability.

As mentioned earlier, absorbable polymers and medical devices made from such polymers are known in the art. Conventional absorbable polymers include polylactic acid or polylactide, polyglycolic acid or polyglycolide, poly(p-dioxanone), various poly(ether esters), poly(amino acids), copolymers and terpolymers of lactide, glycolide, p-dioxanone, trimethylene carbonate, $\epsilon$-caprolactone, poly(ethylene diglycolate), poly(ethoxyethylene diglycolate), polyethylene glycol in various combinations, etc. The absorbable polymers are designed to have a chemistry such that the polymers breakdown in vivo and are either metabolized or otherwise broken down, for example by hydrolysis, and excreted from the patient's body. The advantages of utilizing implantable medical devices made from absorbable polymers are numerous and include, for example, eliminating the need for additional surgeries to remove an implant after it serves its function. Ideally when a "temporary presence" of the implant is desired, support can be provided until the tissue heals.

Polymer blends of the present invention include poly(p-dioxanone) containing from about 95 mol % to about 99.9 mol % regular molecular weight resin, and about 0.1 mol % to about 5 mol % of ultrahigh molecular weight poly(p-dioxanone), having weight average molecular weight of about 300,000 Daltons or above.

As indicated above, the polymer blends disclosed herein are two component blends of a bioabsorbable polymer, each component selected on the basis of its weight average molecular weight distribution. The first component is selected to possess a weight average molecular weight typically between about 50,000 to about 200,000 Daltons. The second component is selected to possess a weight average molecular weight typically between about 300,000 to about 3,000,000 Daltons.

In another form, the composition comprises a two component blend having a first component of a weight average molecular weight more typically between about 80,000 to about 160,000 Daltons, and preferably between about 100,000 to about 120,000 Daltons, and a second component of a weight average molecular weight more typically between about 300,000 to about 1,000,000 Daltons and preferably between about 350,000 Daltons to about 550,000 Daltons.

The amounts of the first and the second molecular weight distributions in the blends are typically in ratios to each other of between about 95/5 to about 99.9/0.1 (weight/weight) percent, respectively. More typically, this ratio is between 96/4 and 99.5/0.5, respectively. Preferable are bimodal compositions having weight ratios of regular to ultrahigh molecular weight distributions of 98/2 and 99/1, respectively. The ratio of the first and second molecular weight distributions will be at least one to three, or higher ratios (i.e., one to four, one to five, etc.).

In accordance herewith, a medical device may be produced from a blended absorbable polymeric composition of the present invention disclosed herein that exhibits substantially increased rates of crystallization, as compared to the rate of crystallization of a device produced from an individual polymeric component of the blended composition. The medical devices that may be manufactured from the novel blends disclosed herein include, but are not limited to, sutures, clips, staples, pins, screws, fibers, stents, gel caps, tablets, microspheres, meshes, fabrics, clamps, plates, hooks, buttons, snaps, prosthetics, grafts, injectable polymers, vertebrae discs, anchoring devices, suture anchors, septal occlusion devices, injectable defect fillers, preformed defect fillers, bone waxes, cartilage replacements, spinal fixation devices, drug delivery devices, foams and films, and other conventional medical devices and equivalents thereof.

The blended compositions disclosed herein may further comprise a pharmaceutically active agent substantially homogenously mixed with the copolymer blend of the present invention. It is envisioned that the pharmaceutically active agent may be released in a living body organism by mechanisms including diffusion and/or a polymer hydrolysis mechanism. The pharmaceutically active agents include pharmaceutically active agents such as analgesics, anti-inflammatory compounds, muscle relaxants, anti-depressants, anti-viral, antibiotic, anesthetic, and cytostatic compounds. In another form, the analgesics may include acetaminophen or ibuprofen. In yet another form, the anti-inflammatory compounds include compounds selected from the group consisting of non-steroidal anti-inflammatory drugs (NSAIDs), prostaglandins, choline magnesium salicylate, salicyclic acid, corticosteroids, methylprednisone, prednisone, and cortisone, and other conventional pharmaceutically active agents and equivalents thereof.

The methods of making the novel polymeric blend compositions disclosed herein may, in general, comprise a step of blending a first absorbable polymer component having a first molecular weight distribution with a second absorbable polymer component having a second molecular weight distribution. In one form, the blending step is performed by melting the amounts of first and second components in a sufficient quantity at a temperature above the melting point of the highest melting component, so as to ensure forming a substantially homogenous mixture. In another form, the blending step is performed by dissolving the amounts of first and second molecular weight distributions in a sufficient quantity in a suitable solvent, and subsequently, removing the solvent, thereby forming a substantially homogenous mixture. The dissolving step of the method may further comprise selecting a suitable solvent from the group consisting of acetone, ethyl acetate, ethyl lactide, tetraglycol, chloroform, tetrahydrofuran, dimethyl sulfoxide, N-methylpyrolidinone, dibutyl phthalate, methylene chloride, methyl ethyl ketone, dibasic esters, methyl isobutyl ketone, dipropylene glycol, dichloromethane and hexafluoroisopropyl alcohol. The process equipment utilized in manufacturing the blends of the present invention will include conventional polymeric processing equipment such as that described in the following examples.

The ultrahigh molecular weight distribution polymeric components of the blends of the present invention will be manufactured in a conventional manner. For example, by using less initiator and a longer polymerization time, and for some polymerization processes utilizing solid state polymerization as will be described in the teachings of Example 2.

Specific embodiments of the present invention will now be described further, by way of example. While the following examples demonstrate certain embodiments of the invention, they are not to be interpreted as limiting the scope of the invention, but rather as contributing to a complete description of the invention.

EXAMPLES

For the purpose of this invention, experimental data on two different absorbable polymer systems will be described in the following examples. The first system is a physical blend of standard molecular weight poly(p-dioxanone), "PDS", as a major component with the same polymer having ultrahigh molecular weight as a minor component (Examples 1-8). PDS is known to exhibit slow nucleation, but relatively fast crystal growth. The second system is a physical blend of slow crystallizing 75/25 Lac/Cap copolymer as a major component with a small amount (1 wt. %) of ultrahigh molecular weight poly(L(-)-lactide) (Examples 9-13) as a minor component.

In conducting experimental work, several commercially available instruments were utilized. A description of the equipment used follows:

Differential Scanning Calorimetry (DSC)

Overall crystallization rates depend principally on two factors: the concentration of growing spherulites over time (nucleation rate) and the rate of spherulitic growth. As expected, these processes have a measurable effect on calorimetric data. Calorimetric results were generated on a TA Instruments Differential Scanning Calorimeter, Model 2910 MDSC, using dry $N_2$ as a purge gas.

Crystallization studies were conducted using the second heat measurements in the following manner: Non-isothermal DSC crystallization data were obtained for several absorbable polymers after first, melting the copolymers at temperatures about 30° C. higher than the melting point of that component, second, quenching the polymers to about −60° C. or below, and third, conducting the heating step at a constant heating rate of 10° C./min. Again, a dramatic increase in the heat of fusion values (i.e. crystallization rates) were observed for the blends of the present invention compared to individual homopolymers and copolymers using this non-isothermal method.

Crystallization characteristics were also assessed by the isothermal crystallization method. Isothermal crystallization kinetics analysis of the resins and blends of the present invention were conducted using the DSC technique. The dried, heat-treated resins and blends, as will be described in following examples, were placed into a DSC pan and completely melted three minutes at 140° C. for PDS systems, and three minutes at 200° C. for 75/25 Lac/Cap copolymer systems (230° C. for the blend) to remove any nucleation sites present in the samples. Subsequently, tested materials were rapidly cooled/quenched (cooling rate of −60° C./min) to the desired crystallization temperatures. The isothermal method assumes that no crystallization occurs before the sample reaches the test temperature; the data obtained supported this assumption. Crystallization behavior of the resins and blends were characterized over a wide range of temperatures for both polymeric systems. Isothermal crystallization kinetics (at constant temperature) were monitored as a change in heat flow as a function of time. The isothermal heat flow curve was integrated to determine the crystallinity parameters. It is worth noting that the isothermal DSC runs were made in randomized order to avoid any bias.

The development of crystallinity with time can be accessed from the degree of crystallization, $\alpha$, which is expressed by the ratio $$\alpha = \frac{\Delta Ht}{\Delta H\infty} = \frac{\int_0^t \frac{dQ}{dt} dt}{\int_0^\infty \frac{dQ}{dt} dt}$$

where $\Delta Q/\Delta t$ is the respective heat flow; $\Delta Ht$, the partial area between the DSC curve and the time axis at time t; and $\Delta H\infty$, the total area under the peak and corresponds to the overall heat of crystallization. The degree of crystallization, $\alpha$, is then the crystalline volume fraction developed at time t.

After performing the integration of the heat flow/time curve, the crystallization half-time, $t_{1/2}$, can be determined. The crystallization half-time is the time needed to reach 50 percent crystallinity of the total amount developed during the isothermal run. In order to express crystallization kinetics, a reciprocal crystallization half-time was conveniently presented as a function of crystallization temperature. The data from isothermal measurements will be shown later in the examples.

Some supporting evidence was obtained by the conventional Wide Angle X-Ray Diffraction (WAXD) analysis. The WAXD measurements of the produced blends and monofilaments were carried out on a Siemens Hi-Star™ unit using CuK$\alpha$ radiation at the wavelength of 1.542 Å. The instrument was operated at 40 kV and 40 mA with the collimator size of Ø 0.5 mm. The convolution of the X-ray images and the calculation of crystallinity content were conducted using the DIFFRAC PLUS™ software developed by Siemens.

In vitro Breaking Strength Retention (BSR) measurements for monofilaments described in Examples 7 and 8 were conducted at the following in vitro conditions: 8.98 pH buffer solutions maintained at 50.5° C. temperature. The data was used for BSR evaluations in pounds and percentages. At specified time points, the tensile strength of samples was tested using Instron material testing machine. The test parameters were 1 inch gauge length and 1 inch per minute crosshead speed.

Example 1

Synthesis of Poly(p-Dioxanone): Standard Molecular Weight Polymer (PDS)

Into a suitable, conventional 65-gallon stainless steel, oil jacketed reactor equipped with agitation, 164.211 kg of p-dioxanone monomer (PDO) was added along with 509 grams of dodecanol, 164 grams of D&C Violet No. 2 Dye, and 100 grams of a 0.33M solution of stannous octoate in toluene. The reactor was closed and a purging cycle, along with agitation at a rotational speed of 12 RPM in an upward direction, was initiated. The reactor was evacuated to pressures less than 500 mTorr followed by the introduction of nitrogen gas. The cycle was repeated several times to ensure a dry atmosphere.

At the end of the final introduction of nitrogen, the pressure was adjusted to be slightly above one atmosphere. The vessel was heated at a rate of 180° C. per hour until the oil temperature reached approximately 100° C. The oil temperature was held at 100° C. until the batch temperature reached 50° C., at which point the agitator rotation was changed to the downward direction. When the batch temperature reached 90° C., the oil temperature was reset to 95° C. These conditions were maintained, and samples were taken from the vessel to be measured for Brookfield viscosity. When the polymer batch viscosity reached at least 110 centipoise, the batch was ready for discharge. The agitator speed was reduced to 5 RPM, and a pre-heated filter was attached to the vessel discharge port. The polymer was discharged from the vessel into suitable containers, under a nitrogen purge, covered, and transferred into a nitrogen curing oven set at 80° C. A solid state polymerization was initiated for a period of approximately 96 hours; during this step the nitrogen flow into the oven was maintained to minimize degradation due to moisture.

Once the solid state curing cycle was complete, the polymer containers were removed from the oven and allowed to cool to room temperature. The crystallized polymer was removed from the containers, and placed into a freezer set at approximately −20° C. for a minimum of 24 hours. The polymer was removed from the freezer and ground in a conventional Cumberland granulator fitted with a sizing screen to reduce the polymer granules to approximately 3/16 inches in size. The granules were then sieved to remove any "fines" and then placed into a conventional 20 cubic foot Patterson-Kelley tumble dryer.

The dryer was closed and the pressure was reduced to less than 2 mmHg. Once the pressure was below 2 mmHg, dryer rotation was activated at a rotational speed of 6 RPM with no heat for 10 hours. After the 10 hour vacuum period, the oil temperature was set to 95° C. at a heat up rate of 120° C. per hour. The oil temperature was maintained at 95° C. for a period of 32 hours. At the end of this heating period, the batch was allowed to cool for a period of at least 4 hours, while maintaining rotation and vacuum. The polymer was discharged from the dryer by pressurizing the vessel with nitrogen, opening the discharge valve, and allowing the polymer granules to descend into waiting vessels for long term storage. The storage vessels were air tight and outfitted with valves allowing for evacuation so that the resin was stored under vacuum.

The resin was characterized. It exhibited an inherent viscosity of 1.90 dL/g, as measured in hexafluoroisopropanol at 25° C. and at a concentration of 0.10 g/dL. Differential Scanning Calorimetry using a heating rate of 10° C./min revealed a glass transition temperature of about −8° C. (minus eight degrees Celsius), a melting transition at about 114° C., with a heat of fusion of about 88 J/g. Nuclear magnetic resonance analysis confirmed that the resin was the homopolymer poly(p-dioxanone), PDS with a residual monomer content less than 2 percent.

Example 2

Synthesis of Poly(p-Dioxanone): Ultrahigh Molecular Weight Polymer (UHMWPDS)

The synthesis step for ultrahigh molecular weight poly (p-dioxanone), UHMWPDS was the same as described in Example 1 except for utilizing a much lower initiator content (monomer to initiator ratio was 5,500:1) and a longer lasting solid state stage.

The solid state cure was carried on for 14 days at 80° C., followed by grinding, sieving, and a drying procedure. The resulting dried polymer, UHMWPDS had a glass transition temperature of −7.6° C., a melting point of 117° C., and an enthalpy of fusion of 93.2 J/g, as measured by DSC using a heating rate of 10° C./min. The resin had a weight average molecular weight of 330,000 Daltons as determined by GPC method, and exhibited an inherent viscosity of 5.25 dL/g, as measured in hexafluoroisopropanol at 25° C. at a concentration of 0.10 g/dL. Nuclear magnetic resonance analysis confirmed that the resin was poly(p-dioxanone), with a residual monomer level of 0.07 mole %. Wide Angle X-ray Diffraction (WAXD) analysis revealed that the dried resin contains 56 percent crystallinity.

Example 3

Dry Blending of Unimodal PDS Homopolymers

Appropriate amounts of the dried poly(p-dioxanone) of standard weight average molecular weight (Example 1) and ultrahigh weight average molecular weight component (Example 2), both in divided form (ground), were combined in dry blends. These dry blends were produced on a weight basis, depending on the particular application and surgical need. In the present example, the standard poly(p-dioxanone) resin and UHMWPDS were dry blended as described directly below.

Into a clean 3-cubic foot Patterson-Kelley dryer specific amounts of the dried resins of Example 1 and Example 2 were added. The dryer was closed, and the vessel pressure was reduced to less than 200 mTorr. The rotation was started at 7.5 RPM and continued for a minimum period of one hour. The dry blend was then discharged into conventional portable vacuum storage containers, and these containers were placed under vacuum, until ready for the melt blending step.

For the purpose of this invention, blends of this type can be produced in a similar manner with different compositions. Alternately, one may make the blends of the present invention by combining the PDS of normal molecular weight distribution with the UHMWPDS directly in a conventional melt extruder.

Example 4

Melt Blending of Unimodal PDS and UHMWPDS Components

Once the dry blends were produced and vacuum conditioned for at least three days, the melt-blending step was begun. A ZSK-30 twin-screw extruder was fitted with screws designed for melt blending utilizing dual vacuum ports for purposes of volatilizing residual monomer. The screw design contained several different types of elements including conveying, compression, mixing and sealing elements. The extruder was fitted with a three-hole die plate, and a chilled water bath with water temperature set between 4.5° C. and 21° C. was placed near the extruder outlet. A strand pelletizer and pellet classifier was placed at the end of the water bath. The extruder temperature zones were heated to a temperature of 130° C. to 175° C., and the vacuum cold traps were set to −20° C. The pre-conditioned dry blend granules were removed from vacuum and placed in a twin-screw feed hopper under nitrogen purge. The extruder screws were set to a speed of 35 to 45 RPM, and the feeder was turned on, allowing the dry blend to be fed into the extruder.

The polymer melt blend was allowed to purge through the extruder until the feed was consistent, at which point the vacuum was applied to the two vacuum ports. The polymer blend extrudate strands were fed through the water bath and into the strand pelletizer. The pelletizer cut the strands into appropriate sized pellets; it was found that pellets with a diameter of 1 mm and an approximate length of 3 mm sufficed. The pellets were then fed into a conventional classifier. The classifier separated substantially oversized and undersized pellets from the desired size, usually a weight of about 10-15 mg per pellet. This process continued until the entire polymer dry blend was melt blended in the extruder, and formed into substantially uniform pellets. Samples were taken throughout the extrusion process and were measured for polymer characteristics such as inherent viscosity, molecular weight and composition. Once the melt-blending process was completed, the pelletized polymer was placed in polyethylene bags, weighed, and stored in a freezer below −20° C. to await devolatilization of residual monomer.

The polymer melt-blend was then placed into a 3-cubic foot Patterson-Kelley dryer, which was held under vacuum. The dryer was closed and the pressure was reduced to less than 200 mTorr. Once the pressure was below 200 mTorr, dryer rotation was activated at a rotational speed of 10 RPM with no heat for 6 hours. After the 6 hour period, the oil temperature was set to 85° C. at a heat up rate of 120° C. per hour. The oil temperature was maintained at 85° C. for a period of 12 hours. At the end of this heating period, the batch was allowed to cool for a period of at least 4 hours, molecular weight blend compositions of the present invention. The following methods/conditions were used:

a) First heat measurements—a 5 to 10 milligram sample of interest was quenched to −60° C. in a DSC pan equipped with nitrogen purge, followed by the constant heating rate scan of 10° C./min.

b) Second heat measurements—the sample of interest after melting in a DSC pan at 140° C. for three minutes, and followed by a rapid quench (−60° C./min) to −60° C. was then heated at the constant heating rate of 10° C./min to 140° C.

c) Cooling from the melt—the fresh sample of interest was melted in a DSC pan at 140° C. for three minutes, and followed by the constant cooling step of 10° C./min Calorimetric and supporting Wide Angle X-ray Diffraction, WAXD data obtained on the dried samples are presented in Table 2.

TABLE 2

DSC Calorimetric Properties of PDS Control and Inventive Dried PDS/UHMWPDS Blends

| Blend ID | WAXD cryst. (%) | DSC: First Heat Data | | | DSC: Second Heat Data | | | | DSC: Cooling from 140° C. | | |
|---|---|---|---|---|---|---|---|---|---|---|---|
| | | $T_g$ (° C.) | $T_m$ (° C.) | $\Delta H_m$ (J/g) | $T_g$ (° C.) | $T_c$ (° C.) | $T_m$ (° C.) | $\Delta H_m$ (J/g) | $T_c$ (° C.) | $\Delta H_c$ (J/g) | Slope [W/(g×° C.)] |
| Ex.2 | 56.8 | −7.6 | 117 | 93.2 | −9.0 | 43.8 | 104 | 44.2 | 35.3 | 8.0 | 0.00152 |
| 4A | 42.3 | −6.2 | 111 | 64.6 | −9.8 | 38.1 | 107 | 52.3 | 36.4 | 37.2 | 0.03104 |
| 4B | 44.5 | −7.3 | 109 | 67.6 | −10.3 | 37.0 | 106 | 54.1 | 39.9 | 45.2 | 0.04913 |
| 4C | 41.9 | −7.7 | 110 | 66.8 | −10.6 | 37.6 | 106 | 53.3 | 39.8 | 43.9 | 0.04525 |
| 4D | 43.7 | −4.5 | 112 | 64.2 | −10.0 | 36.0 | 106 | 54.1 | 37.3 | 42.1 | 0.03470 | while maintaining rotation and vacuum. The polymer melt-blend pellets were discharged from the dryer by pressurizing the vessel with nitrogen, opening the discharge valve, and allowing the polymer pellets to descend into waiting conventional storage vessels for long term storage. The storage vessels were air tight and outfitted with valves allowing for evacuation so that the inventive resin blend could be stored under vacuum.

The following PDS/UHMWPDS blend combinations were made as listed in Table 1.

TABLE 1

Melt Blends of PDS/UHMWPDS Compositions

| Blend ID | Weight percent of polymer of Example 1 in PDS/UHMWPDS blend | Weight percent of polymer of Example 2 in PDS/UHMWPDS blend | IV of the final blend (dL/g) | Melt Index* (g/10 min) |
|---|---|---|---|---|
| 4A | 100 | 0 | 1.82 | 0.182 |
| 4B | 99 | 1 | 1.82 | 0.196 |
| 4C | 96 | 4 | 1.85 | 0.162 |
| 4D | 90 | 10 | 1.91 | 0.124 |

*Melt Index measurements (MT987 Extrusion Plastometer, Tinius Olsen, Willow Grove, PA, USA) were conducted at 150° C. using 6,600 g weight disc. The die diameter was 0.0260 inches, while the die length was 0.315 inches. The UHMWPDS resin (Example 2) exhibited no flow at these conditions.

Example 5

Calorimetric and Crystallization Evaluation of the Inventive PDS/UHMWPDS Blends

Differential Scanning Calorimetry (DSC) was used to investigate the crystallization kinetics of the bimodal As evident from Table 2, it was unexpectedly discovered that all PDS/UHMWPDS blend compositions (4B, 4C, and 4D) exhibited synergetically faster crystallization rates when compared to those of the individual blend components (Ex. 2 and 4A). First, this is evident from the lower crystallization temperature ($T_C$) values obtained for these blends during the second heat DSC runs (column 7$^{th}$ from the right). Also, during the cooling from the melt experiments, higher crystallization temperature ($T_C$) was detected for these blends, as well as a higher level of crystallinity ($\Delta H_C$), and higher crystallization slope values (the last column in Table 2), all indicate significantly faster crystallization rates for the blends of the present invention.

Example 6

Isothermal Crystallization Kinetics Evaluation of Inventive PDS/UHMWPDS Blends

In attempt to further characterize the ability of the inventive PDS/UHMWPDS blends to crystallize fast, isothermal crystallization measurements were conducted next using the Differential Scanning Calorimetry (DSC) method described earlier in the text.

The standard method of expressing the crystallization rate from the isothermal measurements is the crystallization half-time, $t_{1/2}$. This is the time needed to reach 50 percent crystallinity of the total amount developed during the isothermal run. Conveniently, a reciprocal crystallization half-time was presented in FIG. 1 as a function of crystallization temperature for both controls and inventive PDS/UHMWPDS blends. The higher the $1000/t_{1/2}$ value is, the faster the crystallization rate is at the given crystallization temperature.

It is evident from the isothermal crystallization data presented in FIG. 1, that in most cases the PDS/UHMWPDS blends crystallized synergetically faster than the individual blend components (Ex. 2 and 4A). This is particularly apparent in the lower temperature range, where nucleation is the dominant crystallization process. For instance, the PDS/UHMWPDS blend with the highest amount of ultrahigh molecular weight component (Ex. 4D), at the higher temperature range crystallized equally as fast as the PDS control sample (4A), but in the lower temperature range, where nucleation is the dominant mechanism, this blend composition (4D) crystallized with the fastest rate. This data suggest that the blending of standard molecular weight PDS with UHMWPDS seeds affects the nucleation greatly as the primary mode of crystallization process.

The advantage of the synergetically faster crystallization rates of the inventive PDS/UHMWPDS blends, as shown in both non-isothermal and isothermal measurements, is massively important for various melt processing procedures including extrusion, injection molding, blow molding, and similar. Some of the advantages of medical devices made from this inventive resin may include better mechanical properties, higher achievable molecular orientation, less polymer degradation during melt processing, and more economical processes. As an example of such processes, the monofilament extrusion of these inventive blends will be described in the following sections.

Example 7

2-0 Monofilament Extrusion of PDS/UHMWPDS Blends

Dried PDS/UHMWPDS blends of Example 4A-4D were extruded using a single-screw Jenkins one inch extruder with an 18:1 barrel length (6-6-6 "GP" screw design) equipped with a single grooved feed throat. The die had a diameter of 60 mils and an L/D of 5/1; the die temperature was 115° C. After passing through an air gap of ¼ inch, the extrudate was quenched in a 22° C. water bath. These conditions for 2-0 size fiber were chosen and tested previously to allow for the best fiber properties.

After exiting the water bath, the fiber was subjected to the following conditions. The fiber line was directed toward a first set of unheated godet rolls at a linear speed of 10 fpm. It was noticed that for the faster line speed of 15 and 20 fpm, the control PDS resin (Ex. 4A) could not develop enough crystallinity prior to the drawing stage, exhibiting weak fiber properties. The fiber line was then directed toward a second set of unheated godet rolls operating in most cases at 39 fpm. The fiber line was then directed through a 6-foot hot air oven at 115° C. to a third set of unheated godet rolls; this set of rolls was operating at 60 fpm. The line was then directed through a second 6-foot hot air oven also at 115° C. to a fourth set of unheated godet rolls. This last set of rolls was operating at 54 fpm, which is a lower speed than the previous set of godet rollers allowing the fiber to relax slightly (10%). The overall draw ratio was in most cases was 5.4× except for the control sample 4A. The final draw ratio for each blend composition was chosen to reflect the highest tensile strength achievable. It was immediately noticed that the inventive blend compositions 4B and 4C (1 and 4 wt. % of UHMWPDS, respectively) developed enough crystallinity (nuclei) before a drawing step that the draw point was clearly defined and visible. This, in part, allowed these fibers to be drawn at higher orientation level resulting in stronger fibers.

However, the PDS/UHMWPDS blend composition with 10% of UHMWPDS (Ex. 4D) failed to produce high quality fiber. The surface of the undrawn extrudes was very rough despite continuously increasing extruder's and die temperatures. Even with a die temperature holding at 150° C. the extrudate was observed to be still rough and lumpy. At those extreme processing temperatures the onset of degradation processes was also notable.

This monofilament extrusion went smoothly for the rest of samples with only occasional breaks. Prior to tensile property testing, the fibers were examined "as drawn" (unannealed), and also after annealing. The annealing step was performed at 85° C. for six hours on straight rack (0% rack relaxation). The residual monomer level for all annealed fibers was found to be below 0.1 mole %, as determined by NMR technique. Summary of the important tensile properties data from this study is given in Table 3 below.

TABLE 3

Tensile Properties of Unannealed and Annealed 2-0 Monofilaments Made from Inventive and Non-Inventive PDS/UHMWPDS Compositions; All Fiber Diameters Were Kept at 14.2 mils

| Example ID | Blend ID | Annealing conditions | Max. Draw Ratio | Final Draw Ratio | Straight. Tensile (Lbs.) | Elong. (%) | Knot Tensile (Lbs.) | Young's Modulus (Kpsi) |
|---|---|---|---|---|---|---|---|---|
| 8A-unannealed | Ex. 4A | None | 5.6x | 4.6x | 11.8 | 49 | 7.4 | 194 |
| 8A | Ex. 4A | 85° C./6 hrs | 5.6x | 4.6x | 11.8 | 49 | 7.2 | 237 |
| 8B-unannealed | Ex. 4B | None | 6.0x | 5.4x | 12.8 | 33 | 7.4 | 238 |
| 8B | Ex. 4B | 85° C./6 hrs | 6.0x | 5.4x | 12.9 | 35 | 7.9 | 297 |
| 8C-unannealed | Ex. 4C | None | 6.0x | 5.4x | 14.8 | 31 | 7.7 | 280 |
| 8C | Ex. 4C | 85° C./6 hrs | 6.0x | 5.4x | 14.6 | 32 | 8.0 | 316 |
| 8D-unannealed | Ex. 4D | Failed to produce smooth fibers | | | | | | |

As shown in Table 3, the monofilaments made from the blends of the present invention (8B and 8C) exhibited enhanced mechanical properties, including higher achievable straight tensile strength, higher knot strength, and higher Young's Modulus values, which are related to improved fiber stiffness. The higher stiffness is also indicated by lower elongation-to-break values of fibers from the inventive blend compositions. As noted before, the PDS/UHMWPDS blend composition with 10 wt. % of UHMWPDS (8D) failed to produce the successful fibers.

Example 8

In Vitro BSR Measurements of Inventive and Control 2-0 Annealed Monofilaments

In order to evaluate medically relevant Breaking Strength Retention, BSR properties of produced 2-0 monofilaments, the hydrolytic degradation of selected samples were performed using 8.98 pH buffer solutions that were maintained at 50.5° C. temperature. At specified time points, the tensile strength of the samples was tested using Instron material testing machine.

Figure 2:
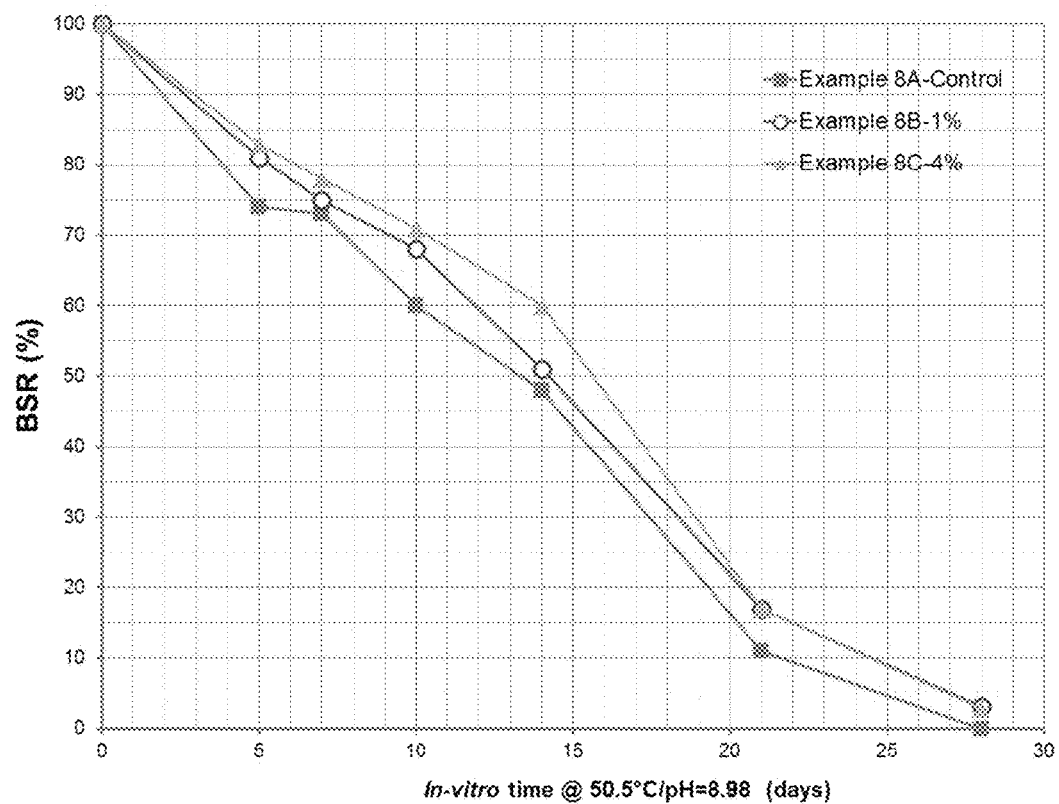
FIG. 2 is a graph that presents in vitro Breaking Strength Retention, BSR properties of PDS control fiber and inventive PDS/UHMWPDS fiber blend compositions.

In FIG. 2, the BSR data are presented in percentages as a function of hydrolysis time for two annealed monofilaments from the inventive blend compositions (8B and 8C) together with PDS control fiber (8A). The results in FIG. 2 clearly indicate longer breaking strength retention for the inventive blend compositions not only from the absolute pound-base calculation, but also on percentage (normalized) strength values.

The stronger fibers with longer BSR profiles have potentially big advantages in medical suture wound closure applications where longer wound support is needed. For instance, these improved long-lasting fibers can find applications as base materials for fully absorbable long term meshes. Also, higher stiffness of the inventive fiber compositions indicates that they may be highly suitable for barbed suture applications, where increased stiffness allows for easier and more precise barb cutting operations.

Example 9

Synthesis of 75/25 Lactide/Caprolactone Copolymer: Standard Molecular Weight Polymer Using a conventional 10-gallon stainless steel oil jacketed reactor equipped with agitation, 6,002 grams of epsilon-caprolactone and 5,052 grams of L(-)-lactide were added along with 16.0 mL of diethylene glycol and 11.55 mL of a 0.33M solution of stannous octoate in toluene. After the initial charge, a purging cycle with agitation at a rotational speed of 10 RPM in a downward direction was initiated. The reactor was evacuated to pressures less than 100 mTorr followed by the introduction of nitrogen gas. The cycle was repeated once again to ensure a dry atmosphere. At the end of the final nitrogen purge, the pressure was adjusted to be slightly above one atmosphere. The rotational speed of the agitator was reduced to 7 RPM in a downward direction. The vessel was heated by setting the oil controller at 195° C. When the batch temperature reached 110° C., rotation of the agitator was switched to the upward direction. The reaction continued for 4 hours from the time the batch temperature reached 180° C.

After the completion of the first stage portion of the polymerization, a very small amount of resin was discharged for analysis purposes; selected characterization was performed. The chemical composition of the prepolymer was 40/60 Lac/Cap mole percent with 0.8 percent of residual monomer as determined by NMR. The DSC data revealed that the prepolymer was fully amorphous with no crystallinity developed, even after additional heat treatment. The glass transition temperature was determined by DSC to be −21° C. (minus 21° C.).

In the second stage, the oil controller set point was set to 190° C., and 18,946 grams of molten L(-)-lactide monomer was added from a melt tank with an agitator speed of 10.0 RPM in a forward direction for 15 minutes. The agitator speed was then reduced to 7.5 RPM in the forward direction. The oil controller was then decreased to 190° C. and the reaction proceeded an additional 3 hours prior to the discharge. At the end of the final reaction period, the agitator speed was reduced to 5 RPM in the downward direction, and the polymer was discharged from the vessel into suitable containers. Alternatively, an underwater pelletization can be performed to make pellets instead of granular material.

Upon cooling, the polymer was removed from the containers and placed into a freezer set at approximately −20° C. for a minimum of 24 hours. The polymer was then removed from the freezer and placed into a Cumberland granulator fitted with a sizing screen to reduce the polymer granules to approximately 3/16 inches in size. The granules were sieved to remove any "fines". The ground polymer (or alternatively pellets) was then placed into a 3 cubic foot Patterson-Kelley tumble dryer to remove any residual monomer. The Patterson-Kelley tumble dryer was closed, and the pressure was reduced to less than 200 mTorr. Once the pressure was below 200 mTorr, the dryer rotation was activated at a rotational speed of 10 RPM with no heat for 18 hours. After the 18 hour period, the oil jacket temperature was set to 60° C. with drying at this temperature for 4 hours. The oil temperature was again raised, this time to 75° C.; this period lasted also 4 hours. Finally, the highest temperature cycle was employed: 110° C. for 20 hours. At the end of the final heating period, the batch was allowed to cool for a period of 2 hours while maintaining rotation and vacuum. The polymer was discharged from the dryer by pressurizing the vessel with nitrogen, opening the discharge valve, and allowing the polymer granules to descend into waiting vessels for long term storage.

The long term storage vessels were air-tight and outfitted with valves allowing for evacuation so that the resin was stored under vacuum. The dried resin exhibited an inherent viscosity of 2.07 dL/g, as measured in hexafluoroisopropanol at 25° C. and at a concentration of 0.10 g/dL. Gel permeation chromatography analysis showed a weight average molecular weight of approximately 122,000 Daltons. Nuclear magnetic resonance analysis confirmed that the resin contained 75 mole percent polymerized L(-)-lactide and 24 mole percent polymerized epsilon-caprolactone, with a residual L(-)-lactide monomer content of about 0.8 percent. The glass transition temperature, $T_g$, of the dried resin was 12.6° C., the melting point was 167° C., and the heat of fusion, $\Delta H_m$, was 27.2 J/g as determined by Differential Scanning Calorimetry using the first heat scan and a heating rate of 10° C./min. Melt index value (200° C./3700 g load) of the dried resin was 0.092 g/10 min.

Example 10

Ultrahigh Molecular Weight Poly(L(-)-Lactide) (UHMW-PLLA)

The ultrahigh molecular weight poly(L(-)-lactide) component, BI Resomer L214 was obtained from Boehringer Ingelheim (Ingelheim am Rhein, Germany) and used without further purification.

Detailed analytical analyses were performed on this resin. The BI Resomer L214 resin exhibited an inherent viscosity of 8.38 dL/g, as measured in hexafluoroisopropanol at 25° C. and at a concentration of 0.10 g/dL. Gel permeation chromatography analysis showed a weight average molecular weight of approximately 543,000 Daltons. Nuclear magnetic resonance analysis confirmed that the resin contained 99.97 mole percent polymerized L(-)-lactide and 0.03 mole residual L(-)-lactide monomer. A melt index value of the dried resin could not be determined due to resin's too high viscosity, regardless of the temperature used. The resin was observed to start to degrade in significant extent before it could flow.

The glass transition temperature, $T_g$, of the dried resin was 70° C., the melting point was 194° C., and the heat of fusion, $\Delta H_m$, was 67 J/g as determined by Differential Scanning Calorimetry using the first heat scan and a heating rate of 10° C./min. However, during the second heat run, the resin exhibited a very slow crystallization rate. Heating from the quench (fully amorphous state) at 10° C./min, the cold crystallization peak was observed at 128° C., melting point at 181° C., and the heat of fusion of only 29 J/g. The resin was kept under vacuum prior further use.

Example 11

Preparation of Physical Blends of 75/25 Lac/Cap Copolymer with 1 wt. % of Ultrahigh Molecular Weight Poly(L(-)-Lactide), UHMWPLLA Dry blending procedure of the 75/25 Lac/Cap copolymer (4,880 g) with the ultrahigh molecular weight poly(L(-)-lactide), PLLA (49 g) was identical to that as described previously in Example 3. Melt blending was also performed using ZSK-30 twin-screw extruder using the steps described earlier in Example 4. The pre-conditioned dry blend granules were removed from vacuum and placed in a twin-screw feed hopper under nitrogen purge. This time the extruder temperature zones were heated to a higher temperature range of 155 to 195° C., and the vacuum cold traps were set to −20° C. The extruder screws were set to a speed of 38 to 40 RPM to allow homogeneous mixing. It is important that the regular and ultrahigh molecular weight components be of the same or very similar chemical structure, such as in this example, to allow for excellent compatibility and homogeneity.

After the completion of the melt blending step, the blend of 75/25 Lac/Cap copolymer with 1 wt. % of UHMWPLLA was sent for drying. The blend was placed into a 3-cubic foot Patterson-Kelley dryer, which was held under vacuum. Following the steps described in Example 4, the resulting blend was dried not only from moisture, but also from any potential monomer that could regenerate during the melt blending procedure.

The resulting dried blend was characterized. The dried blend exhibited an inherent viscosity of 2.01 dL/g, as measured in hexafluoroisopropanol at 25° C. and at a concentration of 0.10 g/dL. Gel permeation chromatography analysis showed a weight average molecular weight of approximately 113,000 Daltons. Nuclear magnetic resonance analysis revealed a residual L(-)-lactide monomer content of 0.42 mole percent. The melt index value (200° C./3700 g load) of the dried resin was 0.090 g/10 min. All these data are similar to those of the major copolymer component (Example 9), indicating very low, if any, polymer degradation during the melt blending step.

The glass transition temperature, $T_g$, of the dried blend was 11.9° C., the melting point was 167° C., and the heat of fusion, $\Delta H_m$, was 28.3 J/g as determined by Differential Scanning Calorimetry using the first heat scan and a heating rate of 10° C./min.

Example 12

Figure 3:
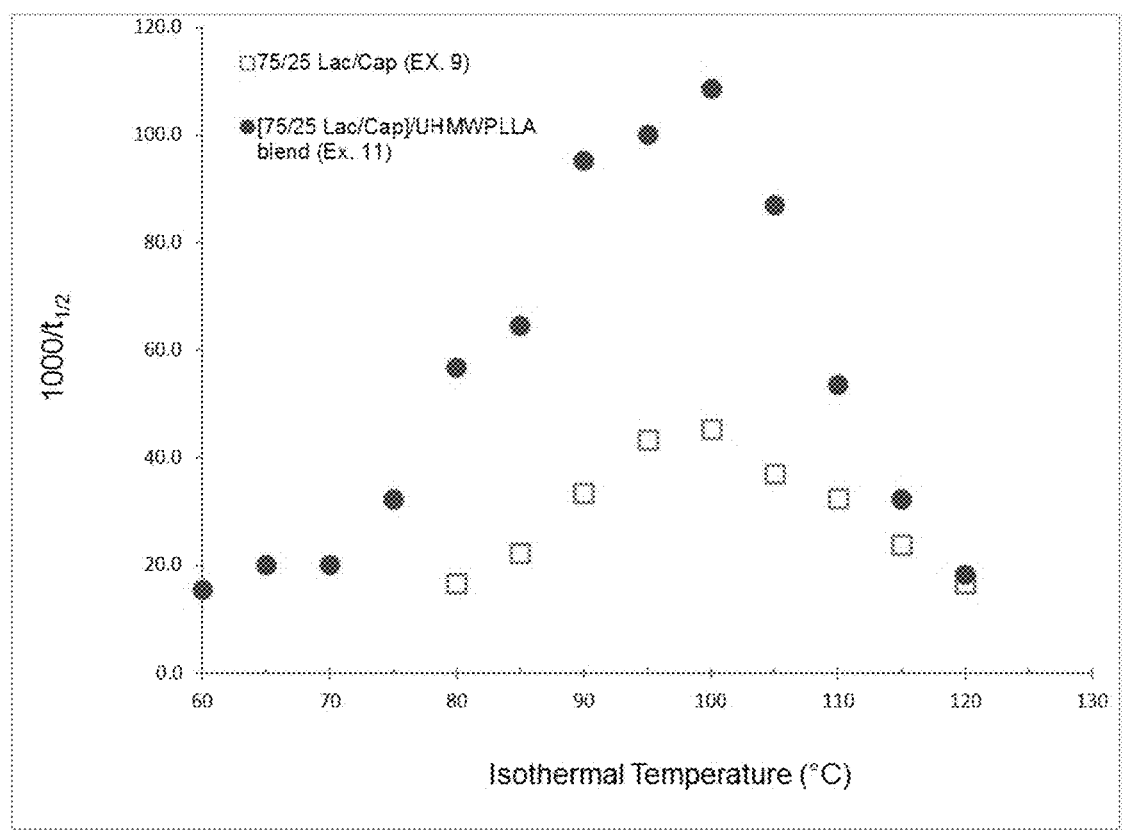
FIG. 3 is a graph that presents isothermal crystallization rates of 75/25 Lac/Cap copolymer and inventive [75/25 Lac/Cap]/UHMWPLLA blend.

Isothermal Crystallization Kinetics Evaluation of Inventive [75/25 Lac/Cap]/UHMWPLLA Blend Isothermal crystallization kinetics of the inventive [75/25 Lac/Cap]/UHMWPLLA blend with 1 wt. % of ultrahigh molecular weight component was carried out using the Differential Scanning Calorimetry (DSC) method described earlier in the Example 6. The blend was melted at 230° C. for three minutes and quenched to the specified isothermal crystallization temperatures. Summary of the isothermal crystallization results for this inventive blend and for the 75/25 Lac/Cap copolymer (Example 9) are presented in FIG. 3.

It was unexpectedly and surprisingly discovered that only 1 (one) weight percent of the UHMWPLLA component produced a dramatic increase in the crystallization kinetics of the inventive blend compared to that of the base 75/25 Lac/Cap copolymer. This was the case for all temperature range studied, from 60° C. to 120° C. It is worth mentioning that these experiments were done under quiescent (non-shear) conditions. A particularly strong effect was observed in the lower temperature region, below 110° C. where nucleation was a dominant crystallization mechanism. Furthermore, it was found that for the lowest temperature runs, from 60° C. to 75° C., the base copolymer, 75/25 Lac/Cap failed to produce any measurable crystallization by this DSC method, while the inventive blend showed still relatively fast kinetics. Even more surprising is the fact that in that lower temperature range (60-75° C.) pure 100% UHMWPLLA was also not able to crystallize, indicating a strong synergetic crystallization effect present in the inventive blend.

The use of fast crystallizing absorbable polymer blends of the present invention may be advantageous during fiber extrusion and drawing processes, such as those used in the manufacture of surgical sutures. Materials exhibiting fast crystallization kinetics generally provide better dimensional stability with greater control of polymer morphology. Drawing of fine fibers is particularly difficult with slow crystallizing polymers, since excessively slow crystallization results in frequently line breaks. The example of the advantageous use of the improved crystallization properties of the inventive blend will be shown next in Example 13 for the monofilament extrusion process.

Example 13

2-0 Monofilament Extrusion of 75/25 Lac/Cap Copolymer and Inventive [75/25 Lac/Cap]/UHMWPLLA Blend Both the dried 75/25 Lac/Cap Copolymer (Example 9) and the inventive [75/25 Lac/Cap]/UHMWPLLA blend of Example 11 were extruded using a single-screw Jenkins one inch extruder with an 18:1 barrel length (6-6-6 "GP" screw design) equipped with a single grooved feed throat. The die had a diameter of 60 mils and an L/D of 5/1; the die temperature was 180° C. for the 75/25 Lac/Cap Copolymer, and much higher, 250° C., for the blend to melt completely UHMWPLLA seeds. After passing through an air gap of ¼ inch, the extrudate was quenched in a 22° C. water bath. These conditions for 2-0 size were chosen and tested previously to allow for the best fiber properties.

After exiting water bath, the fiber was subjected to the following conditions. The fiber line was directed toward a first set of unheated godet rolls at a linear speed of 10 fpm. The fiber line was then directed toward a second set of unheated godet rolls operating at range of 60 to 90 fpm. The fiber line was then directed through a 6-foot hot air oven at 100° C. to a third set of unheated godet rolls; this set of rolls was operating at 100 fpm. The line was then directed through a second 6-foot hot air oven also at 100° C. to a fourth set of unheated godet rolls. This last set of rolls was operating at 95 fpm, which is a lower speed than the previous set of godet rollers allowing the fiber to relax slightly (5%). The overall draw ratio was in most cases was 9.5×, but increased to 11.5× for slower crystallizing base copolymer.

This monofilament extrusion went smoothly for all samples with no breaks. Prior to tensile property testing, the fibers were examined "as drawn" (unannealed), and also after annealing. The annealing step was performed on selected fibers at 70° C. for nine hours on a straight rack (0% rack relaxation). A summary of the important tensile properties data from this study is given in Table 4 below.

TABLE 4

Tensile Properties of Unannealed and Annealed 2-0 Monofilaments Made from the Copolymer of Example 9 and Inventive [75/25 Lac/Cap]/UHMWPLLA Blend Composition of Example 11

| Fiber ID | Resin ID | Diameter (mils) | Max. Draw Ratio | Final Draw Ratio | Straight Tensile (Lbs) | Elong. (%) | Knot Tensile (Lbs) | Young's Modulus (Kpsi) |
|---|---|---|---|---|---|---|---|---|
| 13A | Ex. 9 | 14.18 | 10× | 9.5× | 9.1 | 25 | 4.8 | 559 |
| 13B | Ex. 9 | 14.14 | 11× | 9.9× | 10.4 | 34 | 4.0 | 500 |
| 13C | Ex. 9 | 14.27 | 12× | 11.4× | 11.9 | 26 | 5.7 | 648 |
| 13C-Annealed | Ex. 9 | 14.22 | 12× | 11.4× | 11.6 | 28 | 5.4 | 706 |
| 13D | Ex. 11 | 14.18 | 10× | 9.5× | 12.3 | 33 | 4.4 | 487 |
| 13D-Annealed | Ex. 11 | 14.04 | 10× | 9.5× | 11.9 | 35 | 5.8 | 588 |

It is evident from Table 4 that the tensile properties of the unannealed fiber made from the inventive [75/25 Lac/Cap]/UHMWPLLA blend composition containing 1 wt. % of UHMWPLLA (13D) are superior to those obtained on the base copolymer (13A-C) regardless of the final draw ratio achieved. After annealing of the highly oriented base copolymer sample (13C-Annealed, drawn at final 11.4× ratio), and the inventive blend fiber (13D-Annealed, drawn at final 9.5× ratio), this conclusion still remains. Despite the fact that the 13D-Annealed fiber had a smaller diameter compared to the control 13C-Annealed sample (14.04 vs. 14.22 mils), the fiber from the inventive blend composition exhibited higher straight tensile strength and higher knot strength values. It also displayed higher elongation-to-break values and lower Young's modulus, which all may indicate better fiber pliability or softness.

It has been shown in the previous set of examples that the physical blends of standard molecular weight absorbable polymer as a major component and ultrahigh molecular weight absorbable polymer of the same or similar chemical structure as a minor component significantly increased the crystallization rates under both, non-shear (quiescent) and shear present conditions compared to the same properties found for the individual blend components. This synergetic effect was rather unexpected considering the small amount of the minor, ultrahigh molecular component in the blends. During the fiber extrusion, which is a type of shear-present processing, it was observed that fibers made from the inventive blends exhibited much faster nucleation rates, allowing for higher effective molecular orientation and higher initial tensile strength. In addition, Breaking Strength Retention, BSR data revealed longer hydrolysis/degradation for these blends, making them particularly suitable for long-term medical applications, i.e., for wounds that heal slower.

Another important discovery is the strong crystallization enhancement that was found during non-shear (quiescent) conditions as measured by DSC technique. This allows for much improved polymer processing even in cases where shear forces are limited, or not present to enhance nucleation rates in the polymer resin. Such processes may include compression molding, injection molding of bigger parts, slow throughput film extrusion, rotational molding, etc.

Although this invention has been shown and described with respect to detailed embodiments thereof, it will be understood by those skilled in the art that various changes in form and detail thereof may be made without departing from the spirit and scope of the claimed invention.

We claim:

1. An absorbable semi-crystalline polymer blend composition, comprising:
   (a) a first amount of a first absorbable polymer having a first crystallization rate, a first molecular weight distribution and a weight average molecular weight from about 50,000 to about 200,000 Daltons; and,
   (b) a second amount of a second absorbable ultrahigh molecular weight polymer having a second crystallization rate, a second molecular weight distribution and a weight average molecular weight from about 300,000 to about 3,000,000 Daltons,
   wherein the weight average molecular weight ratio of said first molecular weight distribution to said second molecular weight distribution is at least about one to three and wherein a substantially homogeneous blend of said first and second components is formed in a ratio of between about 99.9/0.1 to about 95/5 weight/weight percent, said substantially homogeneous blend having a crystallization rate greater than each of said first crystallization rate and said second crystallization rate.

2. The absorbable polymer blend composition of claim 1, wherein the first and second components comprise lactide—rich homopolymers and copolymers.

3. The absorbable polymer blend composition of claim 1, wherein the first and second components comprise p-dioxanone—rich homopolymers and copolymers.

4. The absorbable polymer blend composition of claim 1, wherein the first and second absorbable polymers are the same polymer.

5. The absorbable polymer blend composition of claim 1, wherein the first and second absorbable polymers comprise polymers selected from the group consisting of polylactic acid or polylactide, polyglycolic acid or polyglycolide, poly(p-dioxanone), various poly(ether esters), poly(amino acids), copolymers and terpolymers of lactide, glycolide, p-dioxanone, trimethylene carbonate, ϵ-caprolactone, poly(ethylene diglycolate), poly(ethoxyethylene diglycolate), polyethylene glycol, and combinations thereof.

6. A medical device comprising an absorbable semi-crystalline polymer blend composition, said blend composition comprising:
(a) a first amount of a first absorbable polymer having a first crystallization rate, a first molecular weight distribution and a weight average molecular weight from about 50,000 to about 200,000 Daltons; and,
(b) a second amount of a second absorbable ultrahigh molecular weight polymer having a second crystallization rate, a second molecular weight distribution and a weight average molecular weight from about 300,000 to about 3,000,000 Daltons,
wherein the weight average molecular weight ratio of said first molecular weight distribution to said second molecular weight distribution is at least about one to three, and
wherein a substantially homogeneous blend of said first and second components is formed in a ratio of between about 99.9/0.1 to about 95/5 weight/weight percent, said substantially homogeneous blend having a crystallization rate greater than each of said first crystallization rate and said second crystallization rate.

7. The medical device of claim 6 comprising a device selected from the group consisting of sutures, clips, staples, pins, screws, fibers, fabrics, meshes, clamps, plates, hooks, buttons, snaps, prosthetics, grafts, injectable polymers, vertebrae discs, anchoring devices, suture anchors, septal occlusion devices, injectable defect fillers, preformed defect fillers, bone waxes, cartilage replacements, spinal fixation devices, drug delivery devices, a foams, and films.

8. The medical device of claim 6, wherein the first and second components comprise lactide—rich homopolymers and copolymers.

9. The medical device of claim 6, wherein the first and second components comprise p-dioxanone—rich homopolymers and copolymers.

10. The medical device of claim 6, wherein the first and second absorbable polymers are the same polymer.

11. The medical device of claim 6, wherein the first and second absorbable polymers comprise polymers selected from the group consisting of polylactic acid or polylactide, polyglycolic acid or polyglycolide, poly(p-dioxanone), various poly(ether esters), poly(amino acids), copolymers and terpolymers of lactide, glycolide, p-dioxanone, trimethylene carbonate, ε-caprolactone, poly(ethylene diglycolate), poly(ethoxyethylene diglycolate), polyethylene glycol, and combinations thereof.

12. A method of making an absorbable semi-crystalline polymer blend, comprising the step of:
melt processing an absorbable polymer blend, the polymer blend comprising:
(a) a first amount of a first absorbable polymer having a first crystallization rate, a first molecular weight distribution and a weight average molecular weight from about 50,000 to about 200,000 Daltons; and,
(b) a second amount of a second absorbable ultrahigh molecular weight polymer having a second crystallization rate, a second molecular weight distribution and a weight average molecular weight from about 300,000 to about 3,000,000 Daltons,
wherein the weight average molecular weight ratio of said first molecular weight distribution to said second molecular weight distribution is at least about one to three, and
wherein a substantially homogeneous blend of said first and second component is formed in a ratio of between about 99.9/0.1 to about 95/5 weight/weight percent, said substantially homogeneous blend having a crystallization rate greater than each of said first crystallization rate and said second crystallization rate.

13. The method of claim 12, wherein melt-processing includes melt blending, extruding, melt spinning, compression molding, melt blowing or injection molding the blended first and second components at a temperature above their melting temperatures, followed by cooling and crystallizing the blend.

14. The method of claim 12, wherein the first and second components comprise lactide—rich homopolymers and copolymers.

15. The method of claim 12, wherein the first and second components comprise p-dioxanone—rich homopolymers and copolymers.

16. The method of claim 12, wherein the first and second absorbable polymers are the same polymer.

17. The method of claim 12, wherein the first and second absorbable polymers comprise polymers selected from the group consisting of polylactic acid or polylactide, polyglycolic acid or polyglycolide, poly(p-dioxanone), various poly(ether esters), poly(amino acids), copolymers and terpolymers of lactide, glycolide, p-dioxanone, trimethylene carbonate, ε-caprolactone, poly(ethylene diglycolate), poly(ethoxyethylene diglycolate), polyethylene glycol, and combinations thereof.

18. A method of making a medical device, comprising the step of:
forming a medical device by melt-processing or heat treating an absorbable semi-crystalline polymer blend over a temperature range of between about 80° C. to about 260° C., said polymer blend comprising:
(a) a first amount of a first absorbable polymer having a first crystallization rate, a first molecular weight distribution and a weight average molecular weight from about 50,000 to about 200,000 Daltons; and,
(b) a second amount of a second absorbable ultrahigh molecular weight polymer having a second crystallization rate, a second molecular weight distribution and a weight average molecular weight from about 300,000 to about 3,000,000 Daltons,
wherein the weight average molecular weight ratio of said first molecular weight distribution to said second molecular weight distribution is at least about one to three, and
wherein a substantially homogeneous blend of said first and second component is formed in a ratio of between about 99.9/0.1 to about 95/5 weight/weight percent, said substantially homogeneous blend having a crystallization rate greater than each of said first crystallization rate and said second crystallization rate.

19. The method of claim 18, wherein melt-processing includes melt blending, extruding, melt spinning, compression molding, melt blowing or injection molding the blended first and second components at a temperature above their melting temperatures, followed by cooling and crystallizing the blend.

20. The method of claim 18, wherein the first and second components comprise lactide—rich homopolymers and copolymers.

21. The method of claim 18, wherein the first and second components comprise p-dioxanone—rich homopolymers and copolymers.

22. The method of claim 18, wherein the first and second absorbable polymers are the same polymer.

23. The method of claim 18, wherein the first and second absorbable polymers comprise polymers selected from the group consisting of polylactic acid or polylactide, polyglycolic acid or polyglycolide, poly(p-dioxanone), various poly(ether esters), poly(amino acids), copolymers and terpolymers of lactide, glycolide, p-dioxanone, trimethylene carbonate, ε-caprolactone, poly(ethylene diglycolate), poly(ethoxyethylene diglycolate), polyethylene glycol, and combinations thereof.

24. A method of manufacturing a polymeric blend, comprising the steps of:
   (a) providing a first amount of a first absorbable polymer having a first crystallization rate, a first molecular weight distribution and a weight average molecular weight from about 50,000 to about 200,000 Daltons;
   (b) providing a second amount of a second absorbable ultrahigh molecular weight polymer having a second crystallization rate, a second molecular weight distribution and a weight average molecular weight from about 300,000 to about 3,000,000 Daltons, wherein the weight average molecular weight ratio of said first molecular weight distribution to said second molecular weight distribution is at least about one to three, and wherein a substantially homogeneous blend of said first and second components is formed in a ratio of between about 99.9/0.1 to about 95/5 weight/weight percent, said substantially homogeneous blend having a crystallization rate greater than each of said first crystallization rate and said second crystallization rate;
   (c) dry blending the first and second amounts to form a blend;
   (d) drying the blend to remove moisture;
   (e) melt blending the blend to homogeneously distribute the second amount of the second polymer in the first amount of the first polymer to form a substantially homogenous blend; and,
   (f) drying the homogeneous blend to remove moisture and residual monomer.

\* \* \* \* \*